United States Patent [19]

Williams

[11] 4,449,398

[45] May 22, 1984

[54] SHEET PROPERTY SENSOR WITH SHEET WRINKLE REMOVER

[75] Inventor: Paul Williams, Columbus, Ohio

[73] Assignee: Accuray Corporation, Columbus, Ohio

[21] Appl. No.: 391,496

[22] Filed: Jun. 24, 1982

[51] Int. Cl.³ ............................................ G01B 13/06
[52] U.S. Cl. ....................................... 73/159; 73/37.7
[58] Field of Search ........................ 73/37.7, 159, 37.6; 250/572, 571; 356/238

[56] References Cited

U.S. PATENT DOCUMENTS

| | | | |
|---|---|---|---|
| 3,436,853 | 4/1969 | Buss | 38/143 |
| 3,528,002 | 9/1970 | Dunlavey | 324/34 |
| 3,568,341 | 3/1971 | Buss | 38/143 |
| 3,617,872 | 11/1971 | Horn et al. | 324/34 TK |
| 3,818,327 | 6/1974 | Alexander | 324/34 TK |
| 3,827,808 | 8/1974 | Cho | 250/571 X |
| 3,855,524 | 12/1974 | Crawford | 324/34 TK |
| 4,266,142 | 5/1981 | Crawford | 250/572 |
| 4,311,037 | 1/1982 | Gotchel et al. | 73/37.7 X |

FOREIGN PATENT DOCUMENTS 757191  3/1971  Belgium .............................. 73/37.7

Primary Examiner—S. Clement Swisher
Assistant Examiner—Tom Noland
Attorney, Agent, or Firm—C. Henry Peterson

[57] ABSTRACT

Apparatus is provided for sensing a property of a sheet (18). A sensor element (32) is adapted to be placed alongside the sheet path, and a base member (34) is adapted to be positioned on one side of the sheet and in sliding contact with one surface thereof. The sensor element is enabled to produce a sheet property sensing interaction with the sheet in a limited region of the sheet path, the interaction region being movable to any one of a plurality of sensing locations spaced across the width of the sheet. The base member has a pair of groove portions (44, 46) forming gas conducting channels with open sides exposed to the sheet surface in contact with the base member. Each of the groove portions has a part (40, 40A) extending upstream of the interaction region. The groove portions diverge from each other as they extend in a downstream (20) direction. A source of subambient gas pressure communicates with the groove portions for reducing the gas pressure therein so that the contacting surface of the sheet is at least nominally depressed into the groove portions to such an extent that the divergence of the grooves and the longitudinal movement of the sheet exert thereon a transverse tension. This tension is sufficient to substantially smooth out longitudinally extending sheet wrinkles. Typically a plurality of gas removal devices are provided for minimizing the introduction of gas between the base member and the sheet.

6 Claims, 5 Drawing Figures

SHEET PROPERTY SENSOR WITH SHEET WRINKLE REMOVER

TECHNICAL FIELD

This invention relates to apparatus for sensing a property of a traveling sheet. More particularly it relates to apparatus for establishing a reference position for one surface of the sheet in a constantly changing portion thereof while it is undergoing a sensing interaction with a sensing element placed alongside the path of the sheet. Moreover, the invention relates to such apparatus including means for establishing a fixed, predetermined contour for the sheet portion and for precisely maintaining it in a substantially wrinkle-free condition during its exposure to the sensing interaction.

BACKGROUND ART

A great many manufactured sheet materials are produced or modified in one or more continuous operations. In order to control the manufacturing operations, various properties of the sheet material such as its thickness, composition, macrostructure, surface finish, color and the like must be sensed continuously while the sheet is moving rapidly past one or more sensing elements placed alongside the path of the sheet.

The thickness or caliper of moving sheets is commonly measured by passing the sheet over a base member or reference plate on one side of the sheet while a pneumatic surface follower automatically positions itself at a constant distance from the surface of the sheet on the other side. The base member may contain one sensing element such as a magnetic reluctance or eddy current type of proximeter element, while the surface follower may contain another sensing element such as a proximeter target element. The proximeter responds to its distance from the target, and the sheet caliper is derived in effect by subtracting the constant distance of the sheet follower from the surface. A typical arrangement is described in U.S. Pat. No. 3,818,327 to Alexander.

In my copending U.S. Pat. application Ser. No 6/255,424 filed Apr. 20, 1981 and now U.S. Pat. No. 4,434,649 for Improvements in Measuring Apparatus there is described a gauge that is particularly useful for measuring the caliper of paper sheets, utilizing a new and improved surface follower that is capable of normally maintaining its mean distance the one sheet surface constant within a fraction of a micron despite changes in sheet surface roughness or line speed. Up to the present time, however, to my knowledge it has not been possible to maintain the other surface of the sheet in a constant distance relation to the base member with a comparable degree of accuracy and precision, due to the effects of minute wrinkles in the sheet and variations in the thickness of the residual boundary layer of air between the base member and the traveling sheet.

DISCLOSURE OF INVENTION

In accordance with this invention, there is provided apparatus for sensing a property of a sheet that is moving longitudinally along a nominal sheet path, comprising a sensor element adapted to be placed alongside the sheet path, a base member adapted to be positioned on one side of the sheet and in sliding contact with one surface thereof, traversing means for guiding the sensor element and the base member for movement generally along at least one nominal sensor path transverse to the sheet path so that the sensor element is enabled to produce a sheet property sensing interaction with the sheet in a limited region of the sheet path, the interaction region being movable to any one of a plurality of sensing locations spaced across the width of the sheet, the base member having a pair of groove portions forming gas conducting channels with open sides exposed to the sheet surface in contact with the base member, each of the groove portions having a part extending upstream of the interaction region, the groove portions diverging from each other as they extend in the downstream direction, and a source of subambient gas pressure communicating with the groove portions for reducing the gas pressure therein so that the contacting surface of the sheet is at least nominally depressed into the groove portions to such an extent that the divergence of the grooves and the longitudinal movement of the sheet exert thereon a transverse tension sufficient to substantially smooth out longitudinally extending wrinkles from a portion of the sheet at least slightly wider than the interaction region during the approach of the sheet portion thereto.

Typically the apparatus includes a plurality of gas removal means for minimizing the introduction of gas between the base member and the sheet.

The groove portions may be joined upstream of the interaction region to form a continuous groove having reduced gas pressure therein, the continuous groove having the diverging portions extending laterally outwardly of the interaction region.

The apparatus may comprise a further groove encircling the interaction region and located between the region and the diverging groove portions, the further groove also having reduced gas pressure therein.

The apparatus may comprise a scraper for the boundary layer of a gas entrained with the moving sheet, the scraper being located so as to remove from the vicinity of the sheet a substantial portion of the gas constituting the boundary layer before a substantial area of contact is established between the sheet and the base member.

The objects of the invention are to provide sheet sensing apparatus wherein a constantly changing portion of the sheet is subjected to an effective wrinkle-removing operation and caused to conform closely to the contour and position of a base member before and during the time that the sheet portion is subjected to a sensing interaction with a sensing element, thereby substantially reducing sensing errors in the measurement of a sheet property that could otherwise result from the presence of wrinkles in the sheet and its lack of conformity to an assumed position and shape.

Other objects and advantages will become apparent in the following detailed description of certain specific embodiments of the invention, taken in conjunction with the appended drawings.

BEST MODE FOR CARRYING OUT THE INVENTION

Figure 1:
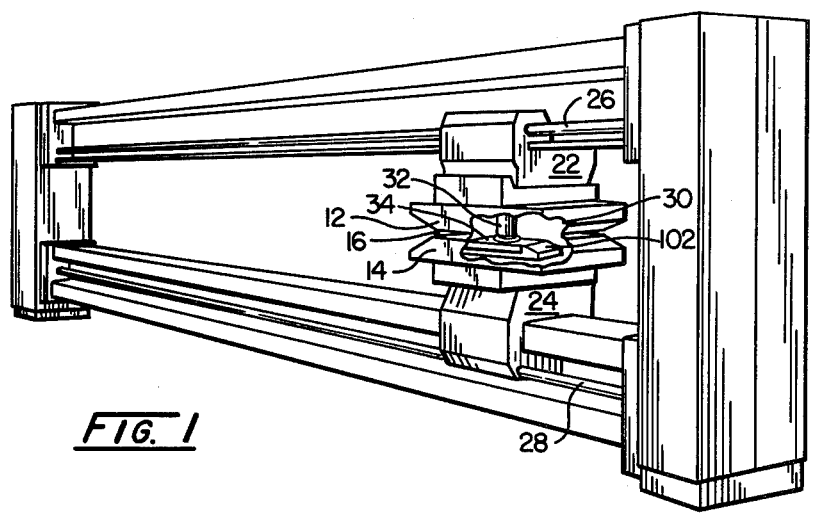
FIG. 1 is a perspective view of a traversing mount for guiding a sensor element and a sensor base member for movement in a predetermined path that is transverse to the path of a traveling sheet.

Referring to FIG. 1, there is shown an upper sensor housing 12 and a lower sensor housing 14. The housings are separated by a narrow air gap 16 through which a sheet 18 (FIG. 2) travels while undergoing measurement by sensor elements installed in the housings 12 and 14.

Typically the sheet 18 is a sheet of paper being produced by a paper-making machine (not shown). The sheet 18 commonly has a width W up to about 10.7 meters or so, and may be traveling in the direction of the arrow 20 in a generally planar course between housings 12 and 14 at a linear speed of about 50–1000 meters per minute.

Housings 12 and 14 have respective carriages 22 and 24, supported on tubular guides as at 26 and 28 which permit traversing the housings 12 and 14 across the width W of the sheet 18.

Figure 2:
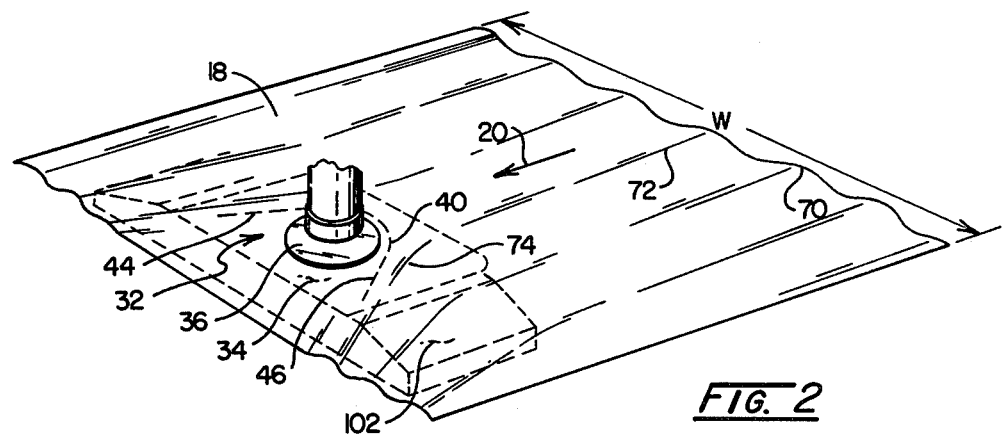
FIG. 2 is a perspective view of a traveling sheet in its spatial relationship to the sensor base member and the sensing elements shown in FIG. 1.

The housings 12 and 14 are shown with a mutual cutaway portion 30 so as to make visible a sensor element 32 contained in housing 12 and a base member 34 contained in housing 14. The sensor element 32 and base member 34, being aboard the traversing housings 12 and 14, are guided for movement generally along at least one sensor path transverse to the path of the sheet 18. The sensor element 32 produces its sheet property sensing interaction with the sheet 18 in a limited region of the sheet path, and the interaction region is movable to any one of a plurality of sensing locations spaced across the width W of the sheet. The specific embodiment of the invention being illustrated is a caliper gauge wherein the sensor element 32 includes a surface follower 36. Hence the interaction region is located directly beneath the surface follower 36 as shown in FIG. 2.

Figure 4:
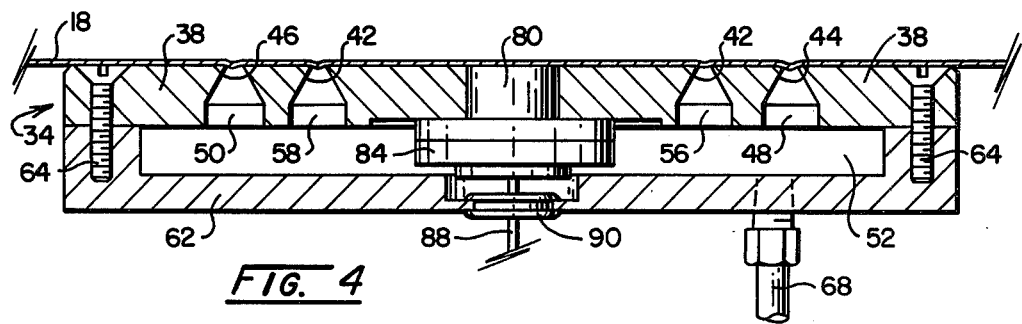
FIG. 4 is a section on the line 4—4 of FIG. 3.
Figure 3:
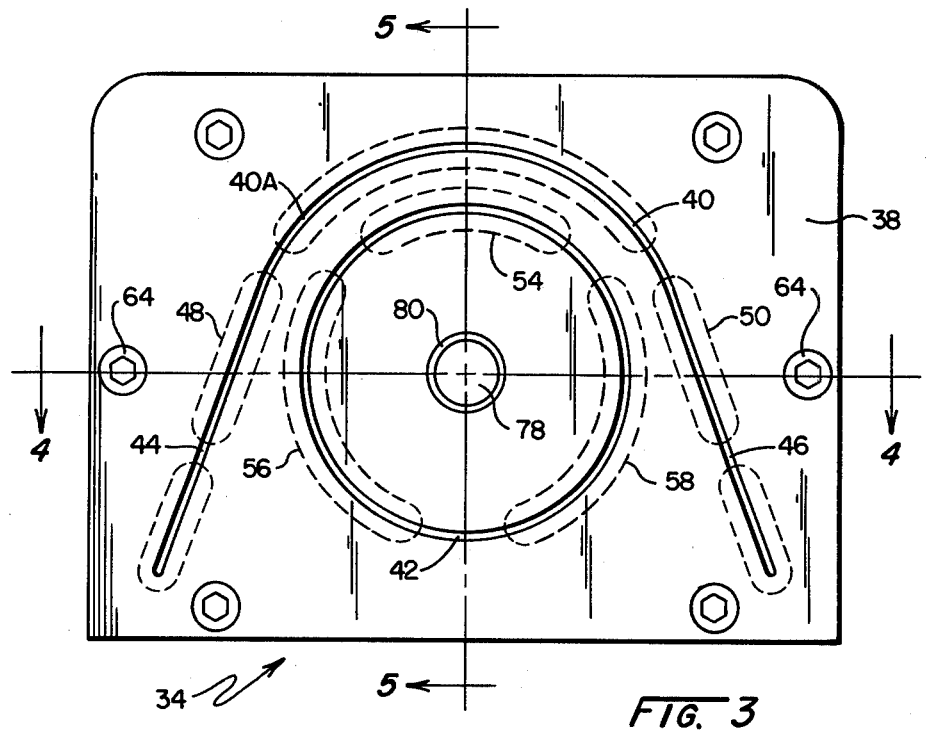
FIG. 3 is a plan view of the base member of FIGS. 1 and 2.
Figure 5:
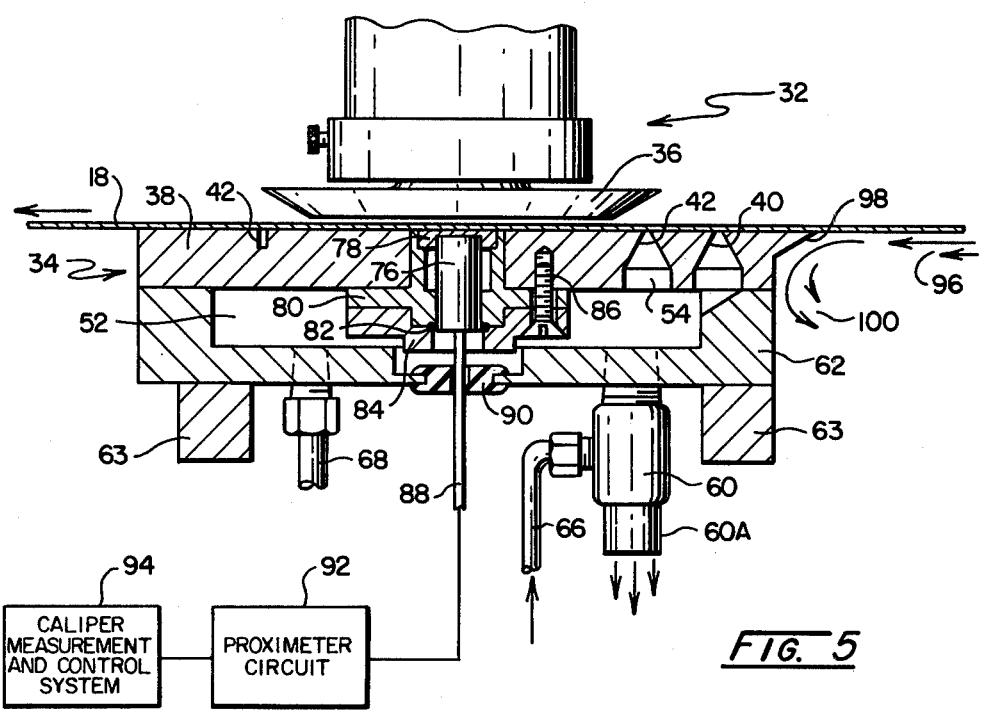
FIG. 5 is a section on the line 5—5 of FIG. 3, also showing a portion of the sheet of FIG. 2 and the sensor element of FIGS. 1 and 2 in the positions they occupy while a portion of the sheet is undergoing a sensor interaction with the sensor element.

As shown in FIGS. 3, 4 and 5 the base member 34 comprises a top plate 38 having two continuous grooves 40 and 42 cut through its top surface that is in contact with the undersurface of the sheet 18. The one groove 42 is circular, whereas the other groove 40 as shown in FIGS. 2 and 3 resembles a conic section with two diverging groove portions 44 and 46. As shown particularly in FIG. 4, these groove portions form gas conducting channels with open sides exposed to the surface of the sheet 18 that is in contact with the base member 34. As shown in FIGS. 2 and 3, each of the groove portions 44 and 46 has a part as seen at 40 and 40A extending upstream (with respect to the direction of sheet 18 travel) of the sheet-sensor interaction region beneath the sheet follower 36. As indicated above, the groove portions 44 and 46 diverge as they extend in the downstream direction.

As shown in FIGS. 3 and 4, the groove portions 44 and 46 widen in some areas into milled parts as at 48 and 50 communicating with a source of subambient gas pressure comprising a plenum 52 (FIGS. 4 and 5). The circular groove 42 widens into similar milled parts as at 54, 56 and 58. During normal sheet sensing operation, the gas pressure (e.g. air pressure) in the plenum 52 is maintained at a negative pressure, with respect to ambient pressure (atmospheric pressure), of about 25–40 centimeters of water.

The pressure reduction system is somewhat similar to that disclosed and claimed in U.S. Pat. No. 3,818,327 Alexander. In the present embodiment, the pressure reduction is effected by a commercial gas flow amplifier 60 (FIG. 5) identified as the Model 901B Transvector (trademark) Jet that is manufactured and marketed by Vortec Corporation, Cincinnati, Oh. The flow amplifier 60 screws into a threaded opening in a plenum plate 62 secured to the bottom of the base member top plate 38 with screws as at 64 (FIG. 4). The plenum plate 62 is in turn secured to mounting rails 63 provided in housing 14, FIG. 1. The gas flow amplifier 60 is typically fed with filtered air, at a positive pressure (above ambient) of about 280 kilopascals (40 psig) fed through a pipe 66. The air exhausted from the plenum 52, together with any particles of sheet-borne debris that pass through the grooves 40 and 42, are ejected through the jet exhaust end 60A.

Larger particles of debris that may happen to lodge on top of the grooves are blown out in the course of periodic or conveniently timed standardizing operations when the sensor element 32 and base member 34 are withdrawn by the traversing mechanism of FIG. 1 to an off sheet position clear of the path of the sheet 18. To this end, a positive pressure is temporarily produced in the plenum chamber 52 by compressed gas (e.g., air) fed in through a pipe 68.

The reduction of pressure in the groove portions 44 and 46 during the sheet sensing operation causes the contacting surface of the sheet 18 to be at least nominally depressed into the groove portions, as is shown in greatly exaggerated fashion in FIG. 4. This depression is not always actually visible or measurable, say, in the case of writing paper moving across the surface of the top plate 38 at normal production speed. In the case of tissue paper moving slowly, the depression is clearly visible. In any case, the depression is sufficient to enable the groove portions 44 and 46 to obtain a grip on the sheet 18 so that the divergence of the grooves and the longitudinal movement of the sheet exert a transverse tension on the sheet. This tension is sufficient to substantially smooth out longitudinally extending wrinkles from a portion of the sheet at least slightly wider than the region of interaction between the sensor element 36 and the sheet 18.

The action is depicted in FIG. 2. Here it can be assumed that the nominal path of the sheet 18 is in a horizontal plane and that the wavy line 70 is the intersection of the sheet 18 with a vertical plane at right angles to the direction of sheet travel. The waviness of line 70 and the shade lines as at 72 and 74 indicate that wrinkles as at 72 are pushed aside as at 74, producing flow lines similar to those found associated with the wake of a boat. As shown between the diverging flow lines, the sheet 18 is laterally "stetched" to make it have a substantially flat contour in a portion of the sheet at least slightly wider than the sheet and sensor interaction region beneath the surface follower 36. The smoothing operation occurs during the approach of the sheet portion to the interaction region, and the transverse tension is maintained to keep the sheet portion smooth until it has passed the interaction region.

As best shown in FIG. 5, in the illustrated embodiment of the invention the sensor element 32 is a compoent of a caliper gauge for continuously measuring the thickness of the sheet 18. The preferred sensor element 32 is particularly the subject of my copending U.S. Pat. application Ser. No. 6/255,424 supra, whose teachings are hereby incorporated by reference. If desired, one can use the element disclosed in U.S. Pat. No. 3,855,524 Crawford. The sensor element 32 includes the pneumatic surface follower or floating head 36, which, during sensor operation, floats at a constant distance of about 0.2 mm above the top surface of the sheet 18.

The surface follower 36 carries a stainless steel or ferrite target piece (not shown) that coacts with a second sensor element comprising a probe coil (not shown) in a coil housing 76. The upper tip of the coil housing 76 is covered by a probe cap 78 constructed of a non-metallic material of a kind that is commonly used for construction of printed circuit boards. The cap 78 is seated in a counterbored opening in the top end of a stainless steel probe retainer 80 and secured thereto with epoxy cement. The bottom end of the coil housing 76 passes through a bored opening in the bottom end of retainer 80 and is gripped by an O-ring 82 that is squeezed between retainer 82 and a probe support 84.

Support 84 is cup-shaped in the middle to receive the protruding lower end of the retainer 80. This arrangement locates the O-ring at the rim of the probe coil housing 76 while allowing room for the countersunk heads of three mounting screws as at 86. Both the retainer 80 and the support 84 are counterbored to accommodate the O-ring 82 in such a way that when the mounting screws as at 86 are tightened, the flattening of the O-ring first causes the O-ring to grip the periphery of the rim of probe housing 76 and then to urge the housing upwardly so as to seat its upper tip end in the probe cap 78.

The electrical leads 88 from the probe coil in housing 76 pass out through a grommet 90 that forms a seal for the plenum 52. The leads 88 are connected to a conventional proximeter circuit 92 whose output signal is supplied to a conventional caliper measurement and control system 94. This arrangement converts the distance of the surface follower 36 from the probe 76 to a measurement of the thickness of the paper 18.

In order for this measurement to be made accurately, not only must the surface follower be able to float at a fixed, constant distance from the top surface of the sheet 18, but also the bottom surface of the sheet must be maintained at a fixed, constant distance from the probe 76, i.e., in flat contact with the top plate 38 of the base member 34. This has been difficult, not only because of the tendency of the sheet 18 to wrinkle but because of problems with a variable-thickness layer of trapped gas (air) between the sheet and the base member.

One source of the trapped air is the boundary layer of air that accompanies the fast-traveling sheet 18. Because of the narrow gap 16 (FIG. 1), typically about 1.3 cm, between the housings 12 and 14, probably all of the turbulent flow and the major portion of the laminar flow are knocked off by the housings 12 and 14. There is, however, a substantial remaining laminar flow next to the sheet 18, as represented by the arrows 96 in FIG. 5, which may have an average velocity of perhaps half the sheet velocity, and which tends to squeeze a layer of air between the sheet 18 and the top plate 38.

To substantially prevent this air from reaching the sheet and sensor interaction region below the surface follower 36, there are provided a plurality of gas removal means, in addition to the housings 12 and 14, to minimize the introduction of the gas (air) between the base member 34 and the sheet 18. The first of these gas removal means comprises a boundary layer scraper 98 on the leading edge of the top plate 38 as is best shown in FIG. 5. This removes the bulk of the air entrained with the sheet 18 when it reaches the base member 34, and diverts the air flow downwardly and away from the sheet, as illustrated by the curving arrows 100. This gas removal takes place before a substantial area of contact is established between the sheet 18 and the base member 34.

A second gas removal means is provided by joining the upstream parts 40 and 40A of the groove portions 44 and 46 to form one continuous gas conducting channel connected to the plenum 52. A third gas removal means is provided by encircling the sheet-sensor interaction region with the groove 42 that is also connected to the plenum 52.

While I am not here claiming any one or all of the gas removal means per se, in many cases they can contribute significantly to the performance of a combination such as that herein disclosed as a best mode embodiment of the invention.

In many cases also it is beneficial to use a pair of extender plates as at 102 (FIGS. 1 and 2). These are conventionally made of plastic such as high density polyethylene. They increase the area of support under the sheet 18 and tend to prevent flutter of the sheet from exerting a leverage (through the stiffness of the sheet) that might tend to raise a portion of the sheet above the top surface of the top plate 38 in the sheet-sensor interaction region.

While the invention has been described and illustrated as an electro-pneumatic caliper gauge combination, the invention is obviously useful as a combination using other types of sensors for other sheet properties. For example, various properties of paper such as color, gloss, roughness and the like may be measured with sensors utilizing optical wavelengths of electromagnetic radiation or other radiation in a manner that requires rather precise and accurate positioning of a traveling sheet surface. In such cases, the region of interaction between the sensor element and the sheet may be simply the area where the radiation impinges on, and is reflected or transmitted by, the sheet.

It is thus to be understood that the specific embodiments shown and described are illustrative only and not restrictive, since obviously many changes, modifications and outwardly different embodiments can be made without departing from the spirit and scope of the invention.

What is claimed is:

1. Apparatus for sensing a property of a sheet that is moving longitudinally downstream along a nominal sheet path, comprising a sensor element adapted to be placed alongside the sheet path, a base member adapted to be positioned on one side of the sheet and in sliding contact with one surface thereof, traversing means for guiding the sensor element and the base member for movement generally along at least one nominal sensor path transverse to the sheet path so that the sensor element is enabled to produce a sheet property sensing interaction with the sheet in a limited region of the sheet path, the interaction region being movable to any one of a plurality of sensing locations spaced across the width of the sheet, the base member having a pair of groove portions forming gas conducting channels with open sides exposed to the sheet surface in contact with the base member, each of the groove portions having a part extending upstream of the interaction region with respect to the sheet movement, the groove portions diverging from each other as they extend in the downstream direction with respect to the sheet movement, and a source of subambient gas pressure communicating with the groove portions for reducing the gas pressure therein so that the contacting surface of the sheet is at least nominally depressed into the groove portions to such an extent that the divergence of the grooves and the longitudinal movement of the sheet exert thereon a transverse tension sufficient to substantially smooth out longitudinally extending wrinkles from a portion of the sheet at least slightly wider than the interaction region during the approach of the sheet portion thereto.

2. Apparatus as in claim 1 including a plurality of gas removal means for minimizing the introduction of gas between the base member and the sheet.

3. Apparatus as in claim 2 wherein the groove portions are joined upstream of the interaction region to form a continuous groove having reduced gas pressure therein, the continuous groove having the diverging portions extending laterally outwardly of the interaction region.

4. Apparatus as in claim 2 or claim 3 comprising a further groove encircling the interaction region and located between the region and the diverging groove portions, the further groove also having reduced gas pressure therein.

5. Apparatus as in claim 2 or claim 3 comprising a scraper for the boundary layer of a gas entrained with the moving sheet, the scraper being located so as to remove from the vicinity of the sheet a substantial portion of the gas constituting the boundary layer before a substantial area of contact is established between the sheet and the base member.

6. Apparatus as in claim 5 comprising a further groove encircling the interaction region and located between the region and the diverging groove portions, the further groove also having reduced gas pressure therein.

* * * * *